United States Patent
Madan

(10) Patent No.: US 12,016,889 B2
(45) Date of Patent: Jun. 25, 2024

(54) COMPOSITIONS AND METHODS FOR TREATING OR PREVENTING INTESTINAL PARACELLULAR PERMEABILITY

(71) Applicant: 9 Meters Biopharma, Inc., Raleigh, NC (US)

(72) Inventor: Jay P. Madan, Raleigh, NC (US)

(73) Assignee: 9 Meters Biopharma, Inc., Raleigh, NC (US)

( * ) Notice: Subject to any disclaimer, the term of this patent is extended or adjusted under 35 U.S.C. 154(b) by 236 days.

(21) Appl. No.: 16/971,741

(22) PCT Filed: Feb. 25, 2019

(86) PCT No.: PCT/US2019/019348
§ 371 (c)(1),
(2) Date: Aug. 21, 2020

(87) PCT Pub. No.: WO2019/165345
PCT Pub. Date: Aug. 29, 2019

(65) Prior Publication Data
US 2021/0030814 A1 Feb. 4, 2021

Related U.S. Application Data

(60) Provisional application No. 62/634,518, filed on Feb. 23, 2018.

(51) Int. Cl.
*A61K 35/741* (2015.01)
*A61K 35/76* (2015.01)
*A61K 38/08* (2019.01)

(52) U.S. Cl.
CPC ............ *A61K 35/741* (2013.01); *A61K 35/76* (2013.01); *A61K 38/08* (2013.01)

(58) Field of Classification Search
CPC .................................................. A61K 35/741
See application file for complete search history.

(56) References Cited

U.S. PATENT DOCUMENTS

| 2015/0164978 A1 | 6/2015 | Paterson et al. |
| 2016/0022760 A1 | 1/2016 | Perrow et al. |
| 2016/0052996 A1* | 2/2016 | Grimm .................. A61P 25/00 435/69.6 |

FOREIGN PATENT DOCUMENTS

| WO | 2017109087 | 6/2017 |
| WO | 2017123610 | 7/2017 |

OTHER PUBLICATIONS

Kelesidis et al., Therapeutic Advances in Gastroenterology, 2012; 5(2):111-125 (Year: 2012).*
Vessler et al., Microbiology and Molecular Biology Reviews, 2011; 75(3):423-433 (Year: 2011).*
Filloux, Journal of Bacteriology, 2010; 192(15):3847-3849 (Year: 2010).*
Steward Technology Networks Immunology and Microbiology, 2018; https://www.technologynetworks.com/immunology/articles/lytic-vs-lysogenic-understanding-bacteriophage-life-cycles-308094 (Year: 2018).*
Klein et al., Proc. Natl. Acad. Sci. USA, 1996; 93:7108-7113 (Year: 1996).*
International Search Report and Written Opinion for International Application No. PCT/US2019/019348, dated May 8, 2019, 14 pages.

* cited by examiner

*Primary Examiner* — Brian Gangle
*Assistant Examiner* — Lakia J Jackson-Tongue
(74) *Attorney, Agent, or Firm* — Morgan, Lewis & Bockius LLP

(57) ABSTRACT

The present invention provides methods and compositions for maintaining and improving the integrity of gastrointestinal epithelial tight junctions, thereby helping to maintain healthy paracellular permeability of the GI epithelium. The present invention provides methods and compositions for the treatment or prevention of various conditions that are associated with gastrointestinal paracellular permeability, including various autoimmune conditions, inflammatory liver diseases, as well as inflammatory conditions of the large or small intestines.

13 Claims, No Drawings
Specification includes a Sequence Listing.

```
                            SEQUENCE LISTING

<160> NUMBER OF SEQ ID NOS: 24

<210> SEQ ID NO 1
    <211> LENGTH: 8
    <212> TYPE: PRT
    <213> ORGANISM: Artificial Sequence
    <220> FEATURE:
    <223> OTHER INFORMATION: Synthetic polymer.

<400> SEQUENCE: 1

Gly Gly Val Leu Val Gln Pro Gly
    1               5

<210> SEQ ID NO 2
    <211> LENGTH: 8
    <212> TYPE: PRT
    <213> ORGANISM: Artificial Sequence
    <220> FEATURE:
    <223> OTHER INFORMATION: Synthetic polymer.

<400> SEQUENCE: 2

Gly Arg Val Cys Val Gln Pro Gly
    1               5

<210> SEQ ID NO 3
    <211> LENGTH: 8
    <212> TYPE: PRT
    <213> ORGANISM: Artificial Sequence
    <220> FEATURE:
    <223> OTHER INFORMATION: Synthetic polymer.

<400> SEQUENCE: 3

Gly Arg Val Cys Val Gln Asp Gly
    1               5

<210> SEQ ID NO 4
    <211> LENGTH: 8
    <212> TYPE: PRT
    <213> ORGANISM: Artificial Sequence
    <220> FEATURE:
    <223> OTHER INFORMATION: Synthetic polymer.

<400> SEQUENCE: 4

Gly Arg Val Leu Val Gln Pro Gly
    1               5

<210> SEQ ID NO 5
    <211> LENGTH: 8
    <212> TYPE: PRT
    <213> ORGANISM: Artificial Sequence
    <220> FEATURE:
    <223> OTHER INFORMATION: Synthetic polymer.

<400> SEQUENCE: 5

Gly Arg Val Leu Val Gln Asp Gly
    1               5

<210> SEQ ID NO 6
    <211> LENGTH: 8
    <212> TYPE: PRT
    <213> ORGANISM: Artificial Sequence
```

```
<220> FEATURE:
<223> OTHER INFORMATION: Synthetic polymer.

<400> SEQUENCE: 6

Gly Arg Leu Cys Val Gln Pro Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 7

Gly Arg Leu Cys Val Gln Asp Gly
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 8

Gly Arg Leu Leu Val Gln Pro Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 9

Gly Arg Leu Leu Val Gln Asp Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 10

Gly Arg Gly Cys Val Gln Pro Gly
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 11

Gly Arg Gly Cys Val Gln Asp Gly
1               5

<210> SEQ ID NO 12
<211> LENGTH: 8
<212> TYPE: PRT
<213> ORGANISM: Artificial Sequence
<220> FEATURE:
```

```
<223> OTHER INFORMATION: Synthetic polymer.

<400> SEQUENCE: 12

Gly Arg Gly Leu Val Gln Pro Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 13

Gly Arg Gly Leu Val Gln Asp Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 14

Gly Gly Val Cys Val Gln Pro Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 15

Gly Gly Val Cys Val Gln Asp Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 16

Gly Gly Val Leu Val Gln Asp Gly
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 17

Gly Gly Leu Cys Val Gln Pro Gly
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic polymer.
```

<400> SEQUENCE: 18

Gly Gly Leu Cys Val Gln Asp Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 19

Gly Gly Leu Leu Val Gln Pro Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 20

Gly Gly Leu Leu Val Gln Asp Gly
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 21

Gly Gly Gly Cys Val Gln Pro Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 22

Gly Gly Gly Cys Val Gln Asp Gly
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic polymer.

<400> SEQUENCE: 23

Gly Gly Gly Leu Val Gln Pro Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic polymer.

```
<400> SEQUENCE: 24

Gly Gly Gly Leu Val Gln Asp Gly
1               5
```

COMPOSITIONS AND METHODS FOR TREATING OR PREVENTING INTESTINAL PARACELLULAR PERMEABILITY

CROSS-REFERENCE TO RELATED APPLICATIONS

This application is a 371 a National Stage Entry of International Application No. PCT/US19/19348, filed Feb. 25, 2019, which claims the benefit of U.S. Provisional Application No. 62/634,518, filed on Feb. 23, 2018, the entire contents of which are hereby incorporated by reference in their entirety.

BACKGROUND

The intestinal epithelium is the layer of cells that forms the luminal surface of the small and large intestines of the gastrointestinal (GI) tract, and represents the largest interface (more than 400 m$^2$) between the external environment and the internal milieu. The intestinal epithelium has two important functions: absorbing nutrients and providing a barrier against harmful environmental substances such as bacteria, viruses, toxins, and food allergens.

The barrier properties of the intestinal epithelium are regulated by specialized plasma membrane structures known as tight junctions. Alterations in tight junctions can result in disruptions of the intestinal barrier functions and increased intestinal permeability. An intact intestinal barrier prevents the permeation of pathogens, antigens, endotoxins, and other proinflammatory substances into the body, whereas intestinal disintegrity allows their entry, which may trigger or exacerbate local or systemic inflammatory disease.

Accordingly, there is a need for effective treatments for intestinal barrier dysfunction and associated disease.

DETAILED DESCRIPTION

The present invention provides compositions that comprise engineered microorganisms or bacteriophages expressing a heterologous polynucleotide. The polynucleotide encodes larazotide peptide or a derivative thereof. The polynucleotide may further comprise a promoter controlling expression, either in a constitutive or inducible fashion, and in some embodiments may encode a signal peptide at the N-terminus of the larazotide or derivative, thereby directing secretion of the peptide outside the cell. The larazotide or derivative when produced in the gastrointestinal tract after delivery of the microorganism or bacteriophage can result in improved integrity of gastrointestinal epithelial tight junctions, thereby helping to maintain healthy paracellular permeability of the GI epithelium. The compositions of the invention find use for the treatment or prevention of various conditions that are associated with gastrointestinal paracellular permeability, including various autoimmune conditions, inflammatory liver diseases, as well as inflammatory conditions of the large or small intestines.

Larazotide is an eight amino acid peptide that promotes tight junction integrity and reduces paracellular permeability, including of the intestinal epithelium. Larazotide has been investigated for treatment of paracellular permeability in Celiac disease (CD) in conjunction with a gluten free diet (GFD). Larazotide has been investigated for administration three times daily, with orally-administered capsules containing enteric-coated beads, which are intended to release larazotide in the duodenum and jejunum. Larazotide has shown promise for the treatment of CD in conjunction with a GFD. Clinical trials with enteric compositions have suggested a possible inverse-dose response. Attempts to empirically determine impacts on paracellular permeability of the intestinal epithelium in vivo have produced inconsistent results. Khaleghi et al., *The potential utility of tight junction regulation in celiac disease: focus on Larazotide acetate*. Ther Adv Gastroenterol 2016, Vol. 9(1)37-49.

In accordance with embodiments of the invention, larazotide or a derivative thereof is heterologously expressed in a microorganism that is a commensal microorganism of the human gastrointestinal tract, or a microbial species that find conventional use as a probiotic.

For example, the microorganism may be a bacterium or fungus, and exemplary microorganisms include those of the genus *Saccharomyces*, *Lactobacillus*, *Clostridium*, *Streptococcus*, *Staphylococcus*, or *Bifidobacterium*. For example, the microorganism may be a species selected from *Saccharomyces boulardii*, *Lactobacillus rhamnosus*, *Lactobacillus plantarum*, *Clostridium butricum*, non-toxigenic *Clostridium difficile*, *Lactobacillus casei*, *Lactobacillus acidophilus*, *Lactobacillus bulgaricus*, *Streptococcus thermophilus*, *Bifidobacterium bifidum*, *Bifidobacterium longum*, *Bifidobacterium lactis*, *Bifidobacterium infantis*, *Bfidobacterium breve*, and *Streptococcus salivarius*. In some embodiments, a probiotic strain (bacterial or fungal) is engineered for expression and optionally secretion of larazotide or derivative thereof from the cell.

In various embodiments, the microorganism is derived from a commensal microorganism of the human gastrointestinal tract, such as those of the genera *Bacteroides*, *Faecalibacterium*, *Corynebacterium*, *Eubacterium*, *Ruminococcus*, *Peptococcus*, *Peptostreptococcus*, *Escherichia*, or *Helicobacter*. In some embodiments, the microbe is *E. coli*. In some embodiments, the microbe is selected from a Fungal genera of *Candida*, *Saccharomyces*, *Aspergillus*, *Penicillium*, *Rhodotorula*, *Trametes*, *Pleospora*, *Sclerotinia*, *Bullera*, and *Galactomyces*.

The microorganism can be selected in some embodiments to impact particular segments of the small or large intestines, by engineering larazotide (or expression) in species or strains naturally present in the desired region of the GI. For example, for the duodenum and jejunum, the bacterial species may be any of the gram-positive cocci or rods that are typically found at this location (e.g., Streptococci and Lactobacilli). For the jejunum, the microbe may be further selected from *Enterococcus* (e.g., *E. fecalis*), *Corynebacterium*, and the yeast *Candida albicans*. For the ileum or colon, the microorganism is generally selected from an anaerobic gram positive or gram negative commensal species, including *Bacteroides* and coliform bacteria (e.g., *E. coli*). "Coliform bacteria" are defined as rod-shaped, Gram-negative non-spore forming and motile or non-motile bacteria which can ferment lactose with the production of acid and gas when incubated at 35-37° C. Coliform bacteria are universally present in large numbers in the feces of warm-blooded animals.

In some embodiments, a combination of microbial species are used, not only to increase the probability that an engineered microorganism can sustain in the subject's GI for some period of time, but also to impact a plurality of regions of the GI. For example, in some embodiments, at least two microorganisms are engineered for larazotide (or derivative) production, such as Streptococci, Lactobacilli, and coliform bacteria (e.g., *E. coli*).

In some embodiments, one or more engineered microorganisms are spore-forming microorganisms, and in these embodiments can be incorporated into the composition in the form of spores. A bacterial spore is a structure produced by bacteria that is resistant to harsh environmental conditions. Many spore-forming bacteria are contained in the *bacillus* and *clostridium* species, but can be found in other species as well. Bacterial spores are extremely resistant, and germinate under the right conditions.

The polynucleotide generally encodes larazotide or derivative thereof (e.g., in an open reading frame) under control of a promoter providing constitutive or inducible expression in the gastrointestinal tract. In some embodiments, the larazotide or derivative is expressed by a promoter such as T7, T5, T3, or Trc, or a promoter having promoter strength in the host cell equal to or more than the strength of T7, T5, T3, or Trc in *E. coli*. The promoter may be a strong constitutive *E. coli* promoter or a coliphage promoter, or a variant thereof. Deuschle et al., *Promoters of Escherichia coli: a hierarchy of in vivo strength indicates alternate structures*, EMBO J. 5(11): 2987-2994 (1986); http://parts.igem.org/Promoters/Catalog/Ecoli/Constitutive. Various promoters depending on the host species are known in the art. Exemplary Lactobacilli promoters can be designed and/or selected in accordance with McCracken A. et al., *Analysis of promoter sequences from Lactobacillus and Lactococcus and their activity in several Lactobacillus species*, Archives of Microbiology June 2000, Vol. 173. Issue 5-6, pp 383-389.

In an embodiment, the polynucleotide is expressed from a plasmid, which may be a low or high copy number plasmid. In another embodiment, the genes are chromosomally integrated into the genome of the host cell, which may further include tandem repeats of the gene comprising larazotide or derivative. In some embodiments, the larazotide is included on a transposable element, such as a transposon.

In various embodiments, the polynucleotide further encodes a secretory signal at the N-terminus of the peptide, or other amino acid sequence, directing secretion from the bacteria or yeast. In various embodiments, the secretory signal is cleaved by the microbe upon export of the peptide out of the cell.

Depending on the host cell, a suitable secretory signal can be designed. A signal peptide or signal sequence is a short peptide (usually 16-30 amino acids long) present at the N-terminus of newly synthesized proteins that are destined towards the secretory pathway. In prokaryotes, signal peptides direct the newly synthesized protein to the SecYEG protein-conducting channel, which is present in the plasma membrane. A homologous system exists in eukaryotes, where the signal peptide directs the newly synthesized protein to the Sec61 channel, which shares structural and sequence homology with SecYEG. Both the SecYEG and Sec61 channels are commonly referred to as the translocon, and transit through this channel is known as translocation.

The core of the signal peptide contains a long stretch of hydrophobic amino acids (about 5-16 residues long) that has a tendency to form a single alpha-helix. In some embodiments, the signal peptide begins with a short positively charged stretch of amino acids, which may help to enforce proper topology of the polypeptide during translocation. At the end of the signal peptide there is typically a stretch of amino acids that is recognized and cleaved by signal peptidase and therefore named cleavage site. Signal peptidase may cleave either during or after completion of translocation to generate a free signal peptide and a mature protein. In both prokaryotes and eukaryotes signal sequences may act co-translationally or post-translationally.

Signal peptides can be designed based on World Wide Web signalpeptide.de/index.php?m=listspdb_bacteria, which provides a non-comprehensive database of signal peptides for various species.

In some aspects, the invention provides a bacteriophage comprising a polynucleotide encoding a peptide that comprises the amino acid sequence of larazotide (SEQ ID NO: 1) or a derivative thereof. The polynucleotide further comprises a promoter controlling expression of the polynucleotide in a host bacterium, as described. The host bacterium may be of the genus *Saccharomyces, Lactobacillus, Clostridium, Streptococcus*, or *Bifidobacterium*. For example, the host bacteria may be a species selected from *Saccharomyces boulardii, Lactobacillus rhamnosus, Lactobacillus plantarum, Clostridium butyricum*, non-toxigenic *Clostridium difficile, Lactobacillus casei, Lactobacillus acidophilus, Lactobacillus bulgaricus, Streptococcus thermophilus, Bifidobacterium bifidum, Bifidobacterium longum, Bifidobacterium lactis, Bifidobacterium infantis, Bifidobacterium breve*, and *Streptococcus salivarius*.

Generally, the host bacterium is a commensal microorganism of the human gastrointestinal tract, and may belong to the genera *Bacteroides, Faecalibacterium, Eubacterium, Ruminococcus, Peptococcus, Peptostreptococcus, Escherichia*, or *Helicobacter*. In some embodiments, the host bacterium is *E. coli*.

The bacteriophage may further encode a secretory signal at the N-terminus of the peptide (as described), so as to drive secretion of the peptide from the host cell. The secretory signal may be cleaved by the host bacteria upon export of the peptide out of the cell. Various types of bacteriophages may be engineered in accordance with these embodiments, including lytic and lysogenic bacteriophages. In some embodiments, the phage is a lytic phage, allowing release of peptide upon lysis of the host cell, rather than through use of a signal peptide.

Exemplary bacteriophages include those of the order Caudovirales, Siphoviridae, Myoviridae, or Podoviridae.

In some embodiments, the bacteriophage is a coliphage, such as lambda phage, M13, T7, T4, or T3 bacteriophage. In other embodiments, the bacteriophage is *lactobacillus* phage, such as phages infecting *Lactobacillus delbrueckii* subsp. *bulgaricus*, known as Ld3, Ld17, and Ld25A. Casey E., *Molecular Characterization of Three Lactobacillus delbrueckii subsp. bulgaricus Phages*, Appl. Environ. Microbiol. 2014 vol. 80 no. 18 5623-5635. Phages can be engineered to optimize the spectrum of infection. Various other phages have been isolated from human feces, which can be used in accordance with this disclosure. Breitbart M, *Metagenomic Analyses of an Uncultured Viral Community from Human Feces*. J Bacteriol. Vol. 185, No. 20 pages 6220-6223 (2003).

In various embodiments, the peptide comprises the amino acid sequence of larazotide (Gly Gly Val Leu Val Gln Pro Gly) (SEQ ID NO: 1), or in some embodiments, consists of or consists essentially of the amino acid sequence of SEQ ID NO: 1. In some embodiments, the peptide comprises a larazotide derivative having from one to five amino acid substitutions or deletions with respect to SEQ ID NO: 1. In some embodiments, the larazotide is a derivative having 1, 2, 3, 4, or 5 amino acid deletions, insertions, and/or substitutions. Larazotide derivatives are described in U.S. Pat. Nos. 8,785,374, 8,957,032, and 9,279,807, which are hereby incorporated by reference in their entirety.

Exemplary derivatives of larazotide include:

```
                                          (SEQ ID NO: 2)
Gly Arg Val Cys Val Gln Pro Gly;

(SEQ ID NO: 3)
Gly Arg Val Cys Val Gln Asp Gly;

(SEQ ID NO: 4)
Gly Arg Val Leu Val Gln Pro Gly;

(SEQ ID NO: 5)
Gly Arg Val Leu Val Gln Asp Gly;

(SEQ ID NO: 6)
Gly Arg Leu Cys Val Gln Pro Gly;

(SEQ ID NO: 7)
Gly Arg Leu Cys Val Gln Asp Gly;

(SEQ ID NO: 8)
Gly Arg Leu Leu Val Gln Pro Gly;

(SEQ ID NO: 9)
Gly Arg Leu Leu Val Gln Asp Gly;

(SEQ ID NO: 10)
Gly Arg Gly Cys Val Gln Pro Gly;

(SEQ ID NO: 11)
Gly Arg Gly Cys Val Gln Asp Gly;

(SEQ ID NO: 12)
Gly Arg Gly Leu Val Gln Pro Gly;

(SEQ ID NO: 13)
Gly Arg Gly Leu Val Gln Asp Gly;

(SEQ ID NO: 14)
Gly Gly Val Cys Val Gln Pro Gly;

(SEQ ID NO: 15)
Gly Gly Val Cys Val Gln Asp Gly;

(SEQ ID NO: 16)
Gly Gly Val Leu Val Gln Asp Gly;

(SEQ ID NO: 17)
Gly Gly Leu Cys Val Gln Pro Gly;

(SEQ ID NO: 18)
Gly Gly Leu Cys Val Gln Asp Gly;

(SEQ ID NO: 19)
Gly Gly Leu Leu Val Gln Pro Gly;

(SEQ ID NO: 20)
Gly Gly Leu Leu Val Gln Asp Gly;

(SEQ ID NO: 21)
Gly Gly Gly Cys Val Gln Pro Gly;

(SEQ ID NO: 22)
Gly Gly Gly Cys Val Gln Asp Gly;

(SEQ ID NO: 23)
Gly Gly Gly Leu Val Gln Pro Gly;
and (SEQ ID NO: 24)
Gly Gly Gly Leu Val Gln Asp Gly.
```

In some embodiments, the derivative comprises the sequence of any one of SEQ ID NOS: 2 to 24 (which may optionally be encoded with an N-terminal secretory signal), or may comprise one, two, three, or four deletions, insertions, and/or substitutions with respect to any one of SEQ ID NOS: 2 to 24.

In some embodiments, the engineered microorganism or phage encodes from 2 to 10 peptides (e.g., 2 to 5 peptides) that are selected from larazotide and its derivatives, including from those shown above.

In some embodiments, larazotide or its derivatives are fused in head-to-tail or head-to-head fashion, to make longer peptides with better expression and/or activity profiles. For example, in some embodiments the microorganism or phage encodes a protein that comprises from 2 to 10 copies of larazotide (and/or a derivatives) in head-to-head and/or head-to-tail arrangement. In some embodiments, these arrangements further include protease cleavage sites, such that monomeric and/or dimeric larazotide (or derivatives) are formed in the gut milieu upon release from the cell.

In some aspects, the invention provides a method for preventing or treating intestinal epithelial paracellular permeability. The method comprises administering the microbe or bacteriophage disclosed herein to the gastrointestinal tract of a subject in need. The microbe or bacteriophage may be ingested by the subject, including in the form of tablets and capsules, or in the form of probiotic-containing foods or nutritional supplements. For example, the composition may be administered in a pharmaceutically acceptable ingestible formulation, such as in a capsule, or may be administered by consuming the engineered microorganism or phage in a supplemented food. In some embodiments, the composition is administered by enema.

The microorganism or bacteriophage may be administered at least once per day once per week, once every two weeks, or once per month. For example, the microbe or bacteriophage may be administered from 1 to 10 times per month, as needed to maintain the production of the peptide in the gastrointestinal tract of the subject. In some embodiments, the microbe or bacteriophage is administered first on a more frequent basis (e.g., from 2 to 7 times per week) for a plurality of weeks, and then on a less frequent basis for maintenance therapy, such as once per week or less (e.g., once or twice per month).

The invention provides for the treatment or prevention of various conditions, including the prevention of disease progression. In some embodiments, the invention results in disease regression or remission. In some embodiments, the subject has leaky gut syndrome, which can be associated with various immunological and inflammatory conditions. In some embodiments, the methods result in repair of tissue damage and barrier integrity associated with chronic inflammatory conditions of the large or small intestines.

In some embodiments, the subject has Celiac Disease. Celiac disease is a genetic autoimmune disease triggered by the ingestion of gluten (a protein in wheat, rye, and barley). Individuals with celiac disease have increased intestinal permeability (e.g., of one or more of the duodenum, jejunum, and ileum), which allows gluten break-down products (the triggering antigens of celiac disease) to reach gut-associated lymphoid tissue, thus initiating an inflammatory response including inflammatory cytokine release and T-cell recruitment. Celiac disease is characterized by chronic inflammation of the small intestinal mucosa that may result in atrophy of the small intestinal villi and diverse symptoms, such as malabsorption, diarrhea, abdominal pain, bloating, and nausea. In addition, celiac disease is also associated with neurological and psychiatric disorders including cerebella ataxia, brain atrophy, peripheral neuropathy, epilepsy, cognitive-function deterioration, depression, and anxiety. Altogether, these symptoms result in a significant reduction in the quality of life for celiac disease patients. No pharmacological therapies are currently available for the treatment of celiac disease. Rather, the only treatment option for celiac disease patients is a life-long adherence to a gluten-free diet (GFD). However, changes in dietary habits are difficult to maintain, and entirely gluten-free food products are not widely available. As such, inadequate dietary compliance is common among celiac disease patients. Long-term consequences for poor dietary compliance include the risk of developing osteoporosis, stomach, esophageal, or colon cancer, and T cell lymphoma. In addition, the continuous gastrointestinal symptoms often result in significant morbidity with a substantial reduction in the quality of life for celiac disease patients. Further still, about 10% of patients diagnosed with celiac disease do not get better on a gluten-free diet, and thus are non-responsive to GFD, or have refractory celiac disease. In some embodiments, the subject has non-responsive or refractory celiac disease.

In some embodiments, the subject has an Inflammatory Bowel Disease (IBD) such as Crohn's Disease or ulcerative colitis.

Crohn's disease may affect any part of the gastrointestinal tract, including the small and large intestine. Complications may occur outside the gastrointestinal tract and may include anemia, skin rashes, arthritis, inflammation of the eye, and tiredness. While the cause of Crohn's disease is unknown it is believed to be due to a combination of environmental, immune and bacterial factors in genetically susceptible individuals. It results in a chronic inflammatory disorder, in which the body's immune system attacks the gastrointestinal tract possibly directed at microbial antigens. Diagnosis is based on a number of findings including biopsy and appearance of the bowel wall, medical imaging and description of the disease. There are no medications or surgical procedures that can cure Crohn's disease. Treatment options help with symptoms, maintain remission, and prevent relapse, and include corticosteroid and methotrexate, which can be used in conjunction with the present invention.

Ulcerative colitis (UC) is a long-term condition that results in inflammation and ulcers of the colon and rectum. The primary symptom of active disease is abdominal pain and diarrhea mixed with blood. Weight loss, fever, and anemia may also occur. Often symptoms come on slowly and can range from mild to severe. Symptoms typically occur intermittently with periods of no symptoms between flares. Complications may include megacolon, inflammation of the eye, joints, or liver, and colon cancer. The cause of UC may involve immune system dysfunction, genetics, changes in the normal gut bacteria, and environmental factors. Several medications are used to treat symptoms including aminosalicylates such as sulfasalazine, steroids, immunosuppressants such as azathioprine, and biological therapy; which may be used in conjunction with the present invention.

In some embodiments, the subject has irritable bowel syndrome (IBS). IBS is a group of symptoms that include abdominal pain and changes in the pattern of bowel movements without any evidence of underlying damage. Disorders such as anxiety, major depression, and chronic fatigue syndrome are common among people with IBS. In various embodiments, the IBS is classified as either diarrhea-predominant (IBS-D), constipation-predominant (IBS-C), or with alternating stool pattern (IBS-A) or pain-predominant.

In some embodiments, the subject has or is at risk of environmental enteropathy (EE) or environmental enteric dysfunction. Environmental enteropathy is an intestinal disorder that occurs among subjects who live in environments with poor sanitation and hygiene. In these subjects, chronic exposure to fecal pathogens is thought to cause inflammation and structural changes in the small intestines such as villous blunting. In children, environmental enteropathy is implicated as a cause of malnutrition, stunted growth, impaired cognitive development, and oral vaccine failure. In various embodiments, methods of the invention reduce, ameliorate, or eliminate one or more symptoms of environmental enteropathy. In some embodiments, the methods result in repair of tissue damage and barrier integrity associated with environmental enteropathy.

In some embodiments, the present methods provide for administration of the larazotide (or derivative) to a subject living in environments of poor sanitation, to treat, prevent, or reduce the incidences of environmental enteropathy. In some embodiments, the present methods provide for administration of the larazotide (or derivative) to subjects chronically exposed to fecal pathogens, who are therefore at risk of developing environmental enteropathy. In these embodiments, the invention can reduce the incidence of EE.

In some embodiments, the subject has or is at risk of necrotizing enterocolitis (NEC). NEC is a medical condition primarily seen in premature infants, and is characterized by variable damages to the intestinal lining, ranging from mucosal injury to full-thickness necrosis and perforation. The presence and severity of necrotizing enterocolitis is graded using the staging system of Bell et al., *J. Ped. Surg.*, 15:569 (1980). In various embodiments, the subject has Stage I NEC, or suspected NEC, or is at risk of NEC, and the regimen is effective to slow or prevent progression of the subject's condition.

In some embodiments, the patient is a pediatric human subject (e.g., for the prevention or treatment of environmental enteropathy or necrotizing enterocolitis). In various embodiments, the pediatric subject is a new born or infant, and may be from about 1 day to about 1 week old, from about 1 week to about 1 month old, from about 1 month to about 12 months old. In various embodiments, the pediatric subject is feeding on formula and/or milk. In other embodiments, the patient is from about 12 months to about 18 months old, from about 18 to about 36 months old, from about 1 to about 5 years old, from about 5 to about 10 years old. Thus, the patient may be a pediatric patient under the age of about 15.

In some embodiments, the pediatric subject is a premature infant. For example, the premature infant may be afflicted with or at risk of developing necrotizing enterocolitis, or may have stage I NEC or suspected NEC. In some embodiments, the premature infant is born at less than 37 weeks of gestational age. In other embodiments, the pediatric subject is a full term infant, for example, an infant who is born later than about 37 weeks of gestational age. In various embodiments, the pediatric subject is of low birth weight. In various embodiments, the pediatric subject weighs less than about 5 pounds, about 4 pounds, about 3 pounds, or about 2 pounds. The Larazotide (or derivative) regimen described herein when administered to a subject having stage I NEC or having suspected NEC, or being at risk for NEC, may reduce the incidence of prenatal asphyxia, shock, sepsis, or congenital heart disease.

In some embodiments, the subject has an inflammatory liver disease. For example, the subject may have or be at risk of a fatty liver disease, such as non-alcoholic fatty acid liver disease (NAFLD) or non-alcoholic steatohepatitis (NASH). The subject in some embodiments has one or more of hepatitis, obesity, diabetes, insulin resistance, hypertriglyceridemia, or glycogen storage disease.

In various embodiments, the regimen of Larazotide (or derivative) prevents progression of the disease, and/or reduces symptoms of the disease, and in some embodiments, allows for liver regeneration.

In some embodiments, the patient presents with liver injury or inflammation, and/or the patient is at risk for a condition such as NAFLD or NASH. In some embodiments, the patient is diagnosed with NAFLD, and is at risk for NASH. NAFLD represents a spectrum of disease occurring in the absence of alcohol abuse. It is characterized by the presence of steatosis (fat in the liver) and may represent a hepatic manifestation of the metabolic syndrome (including obesity, diabetes and hypertriglyceridemia). The severity of NAFLD ranges from the relatively benign isolated predominantly macrovesicular steatosis (i.e., nonalcoholic fatty liver or NAFL) to non-alcoholic steatohepatitis (NASH). NASH is characterized by the histologic presence of steatosis, cytological ballooning, scattered inflammation and pericellular fibrosis. Hepatic fibrosis resulting from NASH may progress to cirrhosis of the liver or liver failure, and in some instances may lead to hepatocellular carcinoma. In some embodiments, methods of the invention reduce, ameliorate, eliminate, one or more symptoms of NAFLD or NASH, or prevent disease progression. e.g., to liver cirrhosis or liver fibrosis. In some embodiments, method of the invention prevents or slows the progression of NAFLD or NASH to hepatocellular carcinoma or liver failure.

In some embodiments, the patient presents with a condition involving liver injury or inflammation of the liver (e.g., hepatitis). In exemplary embodiments, the hepatitis may be caused by viruses, alcohol, drugs, and the like. In some embodiments, the patient presents with hepatitis A, hepatitis B, hepatitis C, hepatitis D, or hepatitis E, and the regimen slows or prevents progression of the liver injury or inflammation to cirrhosis, hepatocellular carcinoma, or liver failure. In other embodiments, the patient presents with alcoholic hepatitis or autoimmune hepatitis. Symptoms of hepatitis generally include fatigue, flu-like symptoms, dark urine, pale stool, abdominal pain, loss of appetite, unexplained weight loss, and jaundice.

In some embodiments, the subject has ischemic injury to the intestines (e.g., ischemic colitis), which may be caused by an occlusive disease or condition, or in some embodiments a non-occlusive disease or condition. In a further embodiment, the patient is at high risk of developing ischemic injury to the intestines.

In some embodiments, the subject has chronic kidney disease, which can be Stage 1, Stage 2, Stage 3, or Stage 4. Kidney disease can manifest from small changes in kidney function, resulting in low glomerular filtration rate (GFR) measured in ml/min/1.73 $m^2$, which can eventually lead to loss of kidney function and/or kidney failure. In some embodiments, patients with Stage 1 chronic kidney disease have a GFR of 90 ml/min/1.73 $m^2$ or higher, indicating kidney damage with normal kidney function; patients with Stage 2 chronic kidney disease have a GFR of 89 to 60 ml/min/1.73 $m^2$, indicating kidney damage with mild loss of kidney function; patients with Stage 3a chronic kidney disease have a GFR of 59 to 45 ml/min/1.73 $m^2$, indicating mild to moderate loss of kidney function; patients with Stage 3b chronic kidney disease have a GFR of 44 to 30 ml/min/1.73 $m^2$, indicating moderate to severe loss of kidney function: patients with Stage 4 chronic kidney disease have a GFR of 29 to 15 ml/min/1.73 m, indicating severe loss of kidney function: and patients with Stage 5 chronic kidney disease have a GFR of less than 15 ml/min/1.73 $m^2$, indicating total loss of kidney function and/or kidney failure. In further embodiments, patients with chronic kidney disease exhibit high levels of serum creatinine.

In some embodiments, the subject has or is at risk of an autoimmune disease. For example, the subject may have or be at risk of diabetes mellitus, rheumatoid arthritis, multiple sclerosis, spondyloarthropathy, Sjogren's syndrome, or Systemic Lupus Erythematosus.

For example, ankylosing spondylitis (AS) is a type of arthritis involving chronic inflammation of the joints of the spine. Other joints may also be impacted. Various inflammatory conditions are often associated with AS, including inflammation of the eye, bowel, heart, lungs, etc. Back pain is a characteristic symptom of AS, and stiffness of the affected joints generally worsens over time. The underlying AS disease is considered to be autoimmune. The cause of AS is unknown, but may involve a combination of genetic and environmental factors. For example, a large majority of those affected have a specific human leukocyte antigen (HLA-B27). Diagnosis is typically based on the symptoms with support from medical imaging and blood tests.

In some embodiments, Larazotide or a derivative thereof is further administered orally as a tablet or capsule (e.g., as a pharmaceutical active agent) from one to three times daily, optionally before meals.

Larazotide or derivative may be administered in any suitable form, including as a salt. For example, Larazotide may be administered as an acetate salt. Salts of Larazotide (or derivative), including the acetate salt and hydrochloride salt, are described in US 2013/0281384, which is hereby incorporated by reference in its entirety. Alternative salts may be employed, including any pharmaceutically acceptable salt of the peptide such as those listed in Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety. Pharmaceutical composition described herein can take the form of tablets, pills, pellets, capsules, capsules containing liquids, capsules containing multiparticulates, powders, solutions, emulsion, drops, or suppositories, or any other form suitable for use. In various embodiments, the pharmaceutical compositions are formulated as a composition adapted for a mode of administration selected from oral, parenteral, or rectal.

The pharmaceutical composition may formulate and/or deliver the larazotide or derivative to a gastrointestinal location of interest. For example, the compositions may be formulated for targeted delivery to the gastrointestinal tract including the stomach, small intestine, large intestine and rectum including all subsections thereof. By targeting release of the peptide agent in the affected region(s) (e.g. duodenum, jejunum and ileum, colon transversum, colon descendens, colon ascendens, colon sigmoidenum and cecum), tight junction integrity at any portion of the GI can be improved, including in some embodiments, in severely damaged tissue.

In various embodiments, the composition may be formulated to have sustained-release profiles, i.e. slow release of the larazotide or derivative in the body (e.g., GI tract) over an extended period of time. In various embodiments, the composition may be formulated to have a delayed-release profile. i.e. not immediately release the larazotide or derivative upon ingestion: rather, postponement of the release until the composition is lower in the gastrointestinal tract; for example, for release in the small intestine (e.g., one or more of duodenum, jejunum, ileum) and/or the large intestine (e.g., one or more of cecum, ascending, transverse, descending or sigmoid portions of the colon, and rectum). In an embodiment, the pharmaceutical composition is formulated to have a delayed-release profile as described in, for example, U.S. Pat. No. 8,168,594, the entire contents of which are hereby incorporated by reference. In some embodiments, an effective amount of larazotide is released in the ileum to reduce antigenic display to the immune system.

Other aspects and embodiments of the invention will be apparent to the skilled artisan from the above disclosure.

The invention claimed is:

1. A microorganism comprising a polynucleotide encoding a peptide that consists of the amino acid sequence of larazotide (SEQ ID NO: 1), the polynucleotide further comprising a promoter controlling expression of the peptide, wherein the microorganism is a species or strain naturally present in the duodenum and/or jejunum.

2. The microorganism of claim 1, wherein the microorganism is a probiotic species.

3. The microorganism of claim 1, wherein the microorganism is of the genus *Saccharomyces, Lactobacillus, Clostridium, Streptococcus, Bifidobacterium, Enterococcus, Corynebacterium*, or *Candida*.

4. The microorganism of claim 3, wherein the microorganism is a species selected from *Saccharomyces boulardii, Lactobacillus rhamnosus, Lactobacillus plantarum, Clostridium butyricum*, non-toxigenic *Clostridium difficile, Lactobacillus casei, Lactobacillus acidophilus, Lactobacillus bulgaricus, Streptococcus thermophilus, Bifidobacterium bifidum, Bifidobacterium longum, Bifidobacterium lactis, Bifidobacterium infantis, Bifidobacterium breve, Candida albicans*, and *Streptococcus salivarius*.

5. The microorganism of claim 1, wherein the microorganism is a commensal microorganism.

6. The microorganism of claim 1, wherein the polynucleotide further encodes a secretory signal at the N-terminus of the peptide.

7. A bacteriophage comprising a polynucleotide encoding a peptide that consists of the amino acid sequence of larazotide (SEQ ID NO: 1), the polynucleotide further comprising a promoter controlling expression of the peptide in a host bacteria,
wherein the bacteriophage infects a host bacteria naturally present in the duodenum and/or jejunum.

8. The bacteriophage of claim 7, wherein the host bacteria is of the genus *Lactobacillus, Clostridium, Streptococcus, Bifidobacterium, Enterococcus*, or *Corynebacterium*.

9. The bacteriophage of claim 8, wherein the host bacteria is a species selected from *Lactobacillus rhamnosus, Lactobacillus plantarum, Clostridium butyricum*, non-toxigenic *Clostridium difficile, Lactobacillus casei, Lactobacillus acidophilus, Lactobacillus bulgaricus, Streptococcus thermophilus, Bifidobacterium bifidum, Bifidobacterium longum, Bifidobacterium lactis, Bifidobacterium infantis, Bifidobacterium breve*, and *Streptococcus salivarius*.

10. The bacteriophage of claim 7, wherein the host bacteria is a commensal microorganism.

11. The bacteriophage of claim 7, wherein the polynucleotide further encodes a secretory signal at the N-terminus of the peptide.

12. The bacteriophage of claim 7, wherein the bacteriophage is lytic or lysogenic.

13. The bacteriophage of claim 7, wherein the bacteriophage is of the order Caudovirales, Siphoviridae, Myoviridae, or Podoviridae.

* * * * *